United States Patent [19]

Pralus et al.

[11] Patent Number: 4,459,240

[45] Date of Patent: Jul. 10, 1984

[54] PROCESS FOR THE PREPARATION OF PERCARBOXYLIC ACIDS

[75] Inventors: Michèle Pralus, Saint Cyr Au Mont D'Or; Jean-Claude Lecoq, Chaponost; Jean-Pierre Schirmann, Oullins, all of France

[73] Assignee: PCUK Produits Chimiques Ugine Kuhlmann, Courbevoie, France

[21] Appl. No.: 450,002

[22] Filed: Dec. 15, 1982

[30] Foreign Application Priority Data

Jan. 13, 1982 [FR] France ................ 82 00407

[51] Int. Cl.$^3$ .......................... C07C 179/10
[52] U.S. Cl. ................................ 260/502 R
[58] Field of Search ...................... 260/502 R

[56] References Cited

U.S. PATENT DOCUMENTS

| 4,267,124 | 5/1981 | Hardy et al. | 260/502 R |
|---|---|---|---|
| 4,330,485 | 5/1982 | Schirmann | 260/502 R |
| 4,338,260 | 7/1982 | Schirmann | 260/502 R |
| 4,391,753 | 7/1983 | Hardy et al. | 260/502 R |

FOREIGN PATENT DOCUMENTS

| 0004407 | 10/1979 | European Pat. Off. | 260/502 R |
|---|---|---|---|
| 0022396 | 1/1981 | European Pat. Off. | 260/502 R |

*Primary Examiner*—Werren B. Lone
*Attorney, Agent, or Firm*—Pennie & Edmonds

[57] ABSTRACT

Process of preparing substantially anhydrous solutions of percarboxylic acids which comprises reacting hydrogen peroxide contained in an aqueous solution with a water miscible carboxylic acid in the presence of a catalyst and an azeotropic organic solvent, continuously removing the water added with the hydrogen peroxide and formed during the reaction by azeotropic distillation by way of a distillation column, and continuously injecting water into the top of the distillation column during at least the major portion of the reaction time, the quantity of the injected water being less than the quantity of the water removed by azeotrope distillation.

11 Claims, No Drawings

PROCESS FOR THE PREPARATION OF PERCARBOXYLIC ACIDS

FIELD OF THE INVENTION

The invention relates to the preparation of substantially anhydrous organic solutions of percarboxylic acids by the reaction of hydrogen peroxide contained in an aqueous solution with water miscible carboxylic acids.

BACKGROUND OF THE INVENTION

It is well known to produce percarboxylic acids by reaction of hydrogen peroxide with water miscible carboxylic acids. This reaction takes place in the presence of a catalyst and the water introduced with the hydrogen peroxide, and the water formed during the reaction is continuously removed by azeotropic distillation by means of an organic solvent capable of forming a hetero-azeotrope.

The reaction of hydrogen peroxide with carboxylic acids is the equilibrium reaction:

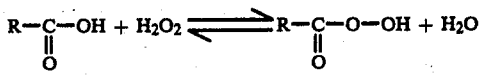  (I)

This reaction should also generally occur at reduced temperatures because of the instability of the percarboxylic acids formed. To accelerate the reaction, catalysts are used which most frequently are strong organic or mineral acids, such as phosphoric acid, sulfuric acid, hydrochloric acid, alkyl or aryl sulfonic acids, trifluoroacetic acid, or acid cationic resins.

To displace the equilibrium of the reaction (I) toward the right, it has been proposed to continuously remove the water by azeotropic distillation (see U.S. Pat. Nos. 2,877,266 and 2,814,641, for example). It is also known that the strong acid catalysts can be advantageously replaced by a boric acid (U.S. Pat. No. 4,338,260) or a metalloid oxide (U.S. Pat. No. 4,330,485).

These processes for preparing percarboxylic acids using hetero-azeotropic distillation of the water during the reaction, however, have a number of significant disadvantages. For example, a significant quantity of the hydrogen peroxide is removed by the azeotropic distillation and ends up in the distilled aqueous phase. Also, the entrained peroxidic oxygen is in the form of untransformed hydrogen peroxide and/or percarboxylic acid. This peroxidic oxygen entrained in the distilled aqueous phase is present regardless of the catalyst used. These losses can reach up to 4% of the hydrogen peroxide initially used in the reaction, as shown by B. Philips et al., in the JOURNAL OF ORGANIC CHEMISTRY, 23, 1823 (1958) and M. Hrusovsky, in CHEMICAL ABSTRACTS, 78, 123937.

In addition to these losses in the distilled aqueous phase by entrainment during the azeotropic distillation, there are also appreciable losses of hydrogen peroxide by decomposition in the azeotropic distillation column. The hydrogen peroxide carried away with the organic-water hetero-azeotrope are subjected to conditions in the distillation column that promote or cause its decomposition. This decomposition of the hydrogen peroxide in the column is accentuated since it no longer contains the stabilizer initially introduced into the reaction mixture by way of the hydrogen peroxide aqueous solution.

The peroxidic oxygen losses due to entrainment and decomposition of the hydrogen peroxide in the azeotropic distillation column make this process of preparing percarboxylic acids economically burdensome.

In all of these prior art processes, the reactor containing the hydrogen peroxide, water, carboxylic acid, the catalyst and the organic solvent acting as the azeotrope entraining agent is below the distillation column which is equipped with a condenser and a decanter. The organic phase is refluxed back into the distillation column after being decanted from the aqueous phase while the decanter aqueous phase is drawn off continuously and discarded.

SUMMARY OF THE INVENTION

The present invention involves the reaction of hydrogen peroxide contained in an aqueous solution with a water miscible carboxylic acid in the presence of a catalyst and an azeotropic organic solvent, continuously removing the water added with the hydrogen peroxide and formed during the reaction by azeotropic distillation, and continuously injecting water into the top of the distillation column over at least a major portion of the reaction time. This process of adding water to the top of the distillation column results in a considerable reduction of the losses of peroxidic oxygen by reason of the azeotropic distillation.

DETAILED DESCRIPTION OF THE INVENTION

The water injected at the top of the distillation column can be pure water or the aqueous phase resulting from the decantation of the condensate of the hetero-azeotrope vapors. In a continuous process part of this aqueous condensate can be continuously recycled to the top of the distillation column. The quantity of water should be such that the liquid recycle has a composition approximating that of the organic solvent-water hetero-azeotrope vapors.

When practicing the invention in a batch or non-continuous operation, the injection of the water should be maintained during the major part of the reaction time. The injection of the water is then stopped and the azeotropic distillation is continued together with the recycle of the organic phase resulting from the condensation of the hetero-azeotrope vapors back into the distillation column until the percarboxylic acid solution in the reactor is substantially or practically anhydrous.

The flow rate of the water injected through the top of the azeotrope distillation column is a function of the composition of the hetero-azeotrope and thus initially depends on the nature of the organic solvent used as the azeotropic entraining agent and in a lesser measure on the functioning pressure of the distillation column, as is apparent to those skilled in the art. The flow rate of the injected water should always be less than the quantity of water drawn off by the condenser, and advantageously is equal to about one-half of the water removed during the reaction by the azeotropic distillation. Thus, continuous operation can easily be employed and results in an organic solution of the percarboxylic acid containing less than about 0.3% of water by weight.

The reinjection of water into the top of the distillation column, which is intended to dehydrate the reaction medium, was not at all obvious and the results flowing from this reinjection of the water were quite unexpected. The reinjection of the water would normally be expected to extend the reaction time and to hinder the displacement of the equilibrium reaction toward the right. Such results, however, do not occur and a number of advantages in applying the process of this invention have, in fact, been established by the applicants. The recycling of part of the condensed water to the top of the azeotrope distillation column to a reaction using sulfuric acid as the catalyst reduces the quantity of the acid catalyst needed to values much below those habitually used by prior art processes while preserving the same reaction speed. Thus, one can use the sulfuric acid catalyst in proportions of 0.0005 to 0.010 mole per mole of hydrogen peroxide while prior art processes require at least ten times this amount to catalyze the reaction and maintain acceptable reaction rate.

Significant reduction in the losses of peroxidic oxygen obtained in accordance with the invention leads to a better utilization of the hydrogen peroxide which is forced back to the foot of the column and thus can be reacted almost quantitatively into percarboxylic acids.

The carboxylic acids with which the invention is concerned are water-miscible aliphatic carboxylic acids, including formic, acetic, propionic and butyric acids.

The azeotropic entraining agent may be selected advantageously from among solvents with a boiling point of less than 100° C. and forming a hetero-azeotrope with water. Solvents containing chlorine, such as chloroform, carbon tetrachloride, methylene chloride, dichloro-1,2 ethane, dichloropropane, solvents containing hydrocarbons, such as cyclohexane, benzene, toluene, esters, such as formates, acetates, propionates, butyrates, isobutyrates of methyl, ethyl, propyl, isopropyl, n-butyl are some non-limiting examples. As previously mentioned, the amount or flow rate of water injected into the top of the column will vary depending upon the entraining agent selected and the optimum amount can readily be determined by routine experimentation.

The temperature at which the reaction is conducted ranges between 40° C. and 100° C. and preferentially between 40° C. and 70° C. Depending on the temperature selected and the reaction system employed, the elimination can be done by operating at atmospheric pressure or under reduced pressure. The pressure may therefore range between 20 mm of mercury and 760 mm of mercury.

The duration of the reaction depends on the nature of the catalyst, the nature of the carboxylic acid, the nature of the azeotropic entraining agent, and the temperature chosen. The reagents may be introduced in equimolecular quantities, but a molar excess or deficiency of one or the other of the reagents can also be utilized. As an indication, from 0.1 to 10 moles of carboxylic acid per mole of hydrogen peroxide can be used, but preferentially from 1 to 5 moles are used.

The reagents can be used in their usual commercial form. Hydrogen peroxide in particular may be employed in the form of commercial aqueous solutions with a titer of 30% to 70% by weight. It may be advantageous to add to the reaction mixture products that stabilize hydrogen peroxide, such as phosphates, polyphosphates, derivatives of ethylenediaminetetraacetic acid, etc.

The solution of percarboxylic acid thus obtained can then serve for the oxidation of a very large number of organic compounds, such as olefins, ketones, amines, aromatic compounds, sulfur derivatives, etc., during a second operation.

The following examples, provided as non-limiting examples, show the application of the process in the invention for the preparation of perpropionic acid catalyzed by sulfuric acid and boric acid. Analogous results are obtained with acetic or butyric acids or with other catalysts, such as strong acid cationic resins or metalloid oxides.

EXAMPLE 1

In a one-liter glass reactor, equipped with a distillation column of 15 Oldershaw plates and a reflux condenser having a decantation system, 630 g. of a solution having the following composition are introduced:
dichloro-1,2-ethane: 20% by weight
propionic acid: 79.95% by weight
sulfuric acid: 0.05% by weight This mixture is brought to a boil so that the liquid flows back under pressure of 100 mm mercury (13.3 kPa). Then, 92 g. of an aqueous solution, 69.6% by weight hydrogen peroxide, also containing 0.8% by weight dipicolinic acid serving as a stabilizer, are introduced in the reactor over a period of 20 minutes. Simultaneously, 25 g/h of water is injected into the top of the distillation column over a period of two hours. The temperature of the reactor is 66° C. The condensed organic phase is recycled into the top of the column to insure the reflux. The condensed aqueous phase is separated by decantation and drawn off continuously.

The reaction is stopped at the end of 2 hours 30 minutes. The distilled aqueous phase, which weights 108 g. contains 0.05% by weight hydrogen peroxide, which represents 0.084% of the quantity of hydrogen peroxide engaged in the reaction.

The percarboxylic acid organic solution obtained contains 24.9% by weight of perpropionic acid, 0.2% by weight of hydrogen peroxide, and 0.11% by weight of water.

The transformation rate of hydrogen peroxide into perpropionic acid is 95.9%. The total hydrogen peroxide loss is only 1.8%.

EXAMPLE 2

636 g. of a solution containing the following is placed in the reactor used in Example 1:
dichloro-1,2-ethane: 19.8% by weight
propionic acid: 79.2% by weight
orthoboric acid: 1.0% by weight The solution is brought to a boil so that the liquid flows back under pressure of 100 mm mercury (13.3 kPa). Then 92 g. of an aqueous solution of 70% by weight of hydrogen peroxide, also containing 0.7% by weight of dipicolinic acid, is introduced in the reactor over a period of 20 minutes. 21 g/h of water is injected continuously at the top of the distillation column over a period of 2 hours, 30 minutes. The temperature of the reactor is 65° C. The vapors of the dichloro-1,2-ethane hetero-azeotrope and water are condensed and decanted. The dichloro-1,2-ethane is sent back to the top of the distillation column while the aqueous phase is drawn off continuously.

The reaction is stopped at the end of 3 hours. The peracid organic solution obtained contains 23.7% by weight of perpropionic acid which represents a transformation rate of 92% of the hydrogen peroxide used. The hydrogen peroxide loss by entrainment in the distillation is 0.12% and the loss by decomposition, 5.4%.

EXAMPLE 3

636 g. of a solution having the following composition are introduced into the reactor used in Example 1:
 dichloro-1,2-ethane: 50.7% by weight
 propionic acid: 48.3% by weight
 orthoboric acid: 1.0% by weight The solution is brought to a boil so that the liquid flows back under pressure of 250 mm mercury (33.3 kPa). Over a period of 15 minutes, 60 g of an aqueous solution containing 69.5% by weight of hydrogen peroxide and 0.8% by weight of dipicolinic acid are passed into the reactor. At the top of the column a total of 42 g. of water is also injected over a period of 2 hours. The temperature of the reactor is 66° C.

The reaction is stopped at the end of 3 hours. The aqueous phase separated after condensation of the hetero-azeotrope vapors weighs 86 g. and contains 1% by weight of hydrogen peroxide which is about 2% of the quantity initially engaged in the reaction.

The organic peracid solution obtained contains 15.4% by weight of perpropionic acid and 0.2% by weight of hydrogen peroxide.

The peracid yield in relation to the hydrogen peroxide is 90.5%. The total loss of hydrogen peroxide by decomposition and entrainment is 6%.

EXAMPLE 4 (comparative example)

Example 3 is reproduced exactly, but omitting the injection of water at the top of the distillation column. Under these conditions, a yield of 84.9% perpropionic acid is obtained in relation to the hydrogen peroxide. The total losses in hydrogen peroxide by decomposition and entrainment reached 10.7%.

We claim:

1. A process for preparing substantially anhydrous solutions of percarboxylic acid which comprises reacting hydrogen peroxide contained in an aqueous solution with a water miscible aliphatic carboxylic acid in the presence of an azeotropic organic solvent having a boiling point of less than about 100° C. and the ability to form a hetero-azeotrope with water, at a temperature between 40° and 100° C. and at a pressure between 20 and 760 mm of mercury, continuously removing the water added with the hydrogen peroxide and formed during the reaction by azeotropic distillation by way of a distillation column, and continuously injecting water into the top of the distillation column during at least the major portion of the reaction time, the quantity of the injected water being less than the quantity of water removed by azeotropic distillation.

2. A process according to claim 1 in which the injected water is pure water.

3. A process according to claim 1 in which part of the water removed from the reaction by condensation of the azeotrope vapors is recycled to the top of the distillation column.

4. The process of claim 3 in which the organic condensate is also recycled to the top of the distillation column and the recycled condensate has approximately the same composition as the vapors of the organic solvent-water azeotrope vapors.

5. A process according to claim 1 in which the injected water is approximately one-half of the water removed from the reaction by the azeotrope distillation.

6. A process according to claim 1 in which the catalyst is a strong acid.

7. A process according to claim 6 in which the strong acid catalyst is sulfuric acid in an amount between about 0.0005 to 0.010 mole per mole of hydrogen peroxide.

8. A process according to claim 5 in which the catalyst is sulfuric acid in an amount between about 0.0005 to 0.010 mole per mole of hydrogen peroxide.

9. A process according to claim 1 in which the catalyst is a metalloid oxide or a boric acid.

10. A process according to claim 4 in which the catalyst is a metalloid oxide or a boric acid.

11. The process according to claim 1 in which the reaction carried out at temperature range between 40° and 70° C.

* * * * *